(12) United States Patent
Novarino et al.

(10) Patent No.: US 11,479,888 B2
(45) Date of Patent: *Oct. 25, 2022

(54) NONWOVEN FABRIC AND PROCESS FOR FORMING THE SAME

(71) Applicant: Fitesa Germany GmbH, Peine (DE)

(72) Inventors: Elena Novarino, Hannover (DE); Florian Teschner, Hannover (DE)

(73) Assignee: Fitesa Germany GmbH, Peine (DE)

( * ) Notice: Subject to any disclaimer, the term of this patent is extended or adjusted under 35 U.S.C. 154(b) by 5 days.

This patent is subject to a terminal disclaimer.

(21) Appl. No.: 16/079,663

(22) PCT Filed: Feb. 27, 2017

(86) PCT No.: PCT/EP2017/054513
§ 371 (c)(1),
(2) Date: Aug. 24, 2018

(87) PCT Pub. No.: WO2017/148865
PCT Pub. Date: Sep. 8, 2017

(65) Prior Publication Data
US 2019/0071802 A1    Mar. 7, 2019

(30) Foreign Application Priority Data

Feb. 29, 2016 (EP) .................................. 16157862

(51) Int. Cl.
*D04H 1/541* (2012.01)
*A61F 13/64* (2006.01)
(Continued)

(52) U.S. Cl.
CPC ........... *D04H 1/5412* (2020.05); *A61F 13/64* (2013.01); *D04H 1/435* (2013.01); *D04H 3/011* (2013.01);
(Continued)

(58) Field of Classification Search
CPC ...... D04H 1/5405; D04H 1/435; D04H 1/485; D04H 1/55; D04H 3/16–163;
(Continued)

(56) References Cited

U.S. PATENT DOCUMENTS 5,620,779 A    4/1997 Levy et al.
6,063,492 A    5/2000 Kurihara et al.
(Continued)

FOREIGN PATENT DOCUMENTS

EP    0 821 044 A2    1/1998
EP    1 181 873 A1    2/2002
(Continued)

OTHER PUBLICATIONS

International Search Report and Written Opinion for International Application No. PCT/EP2017/054513 dated Jun. 17, 2017.

*Primary Examiner* — Larissa Rowe Emrich
(74) *Attorney, Agent, or Firm* — Rimon, P.C.

(57) ABSTRACT

A nonwoven fabric having polylactic acid-containing fibers forming a nonwoven web is provided. The web has a side having an alternating pattern of individualized bonded areas which bonded areas define rods arranged in the cross direction of the web. The rods are arranged so that in the machine direction of the web no uninterrupted regions exist along the web while in the cross direction the arrangement of rods defines uninterrupted regions that extend continuously along the web, the alternating pattern of individualized bonded areas defines a non-bonded area. The web has a basis weight from 5-50 g/m$^2$, the surface of the bonded areas is from 5-20% of the total surface of the side, and the surface of the non-bonded area is from 80-95% of the total surface of the side. Processes for forming the nonwoven fabric and an absorbent article including the nonwoven fabric are also provided.

17 Claims, 2 Drawing Sheets

(51) Int. Cl.
*D04H 1/435* (2012.01)
*D04H 3/011* (2012.01)
*D04H 3/147* (2012.01)
*D04H 3/018* (2012.01)

(52) U.S. Cl.
CPC ........... *D04H 3/147* (2013.01); *D04H 1/5414* (2020.05); *D04H 1/5416* (2020.05); *D04H 3/018* (2013.01)

(58) Field of Classification Search
CPC ................. D04H 3/011; D04H 13/007; D04H 1/54–565; D04H 3/14–153; D10B 2331/041; D10B 2509/026
See application file for complete search history.

(56) References Cited

U.S. PATENT DOCUMENTS

| | | | |
|---|---|---|---|
| 6,506,873 B1* | 1/2003 | Ryan | D01F 6/625 |
| | | | 528/354 |
| 6,677,038 B1 | 1/2004 | Topolkaraev et al. | |
| 6,770,065 B1 | 8/2004 | Sasaki et al. | |
| 2001/0025686 A1* | 10/2001 | Mitsuno | D04H 3/14 |
| | | | 156/229 |
| 2004/0133180 A1 | 7/2004 | Mori et al. | |
| 2004/0241399 A1* | 12/2004 | Marmon | D04H 1/559 |
| | | | 428/196 |
| 2007/0048497 A1* | 3/2007 | Zhou | B32B 5/04 |
| | | | 428/137 |
| 2010/0305543 A1* | 12/2010 | Klaska | A61F 13/51401 |
| | | | 604/391 |
| 2010/0324515 A1* | 12/2010 | Boscolo | D04H 5/06 |
| | | | 604/367 |
| 2012/0227282 A1* | 9/2012 | Hawkinson | A43B 23/0235 |
| | | | 36/87 |
| 2012/0251771 A1* | 10/2012 | Wilson | B29C 55/18 |
| | | | 428/137 |
| 2014/0038487 A1* | 2/2014 | Polosa | D04H 1/492 |
| | | | 442/414 |
| 2014/0276517 A1* | 9/2014 | Chester | A61F 13/539 |
| | | | 604/372 |

FOREIGN PATENT DOCUMENTS

| | | |
|---|---|---|
| EP | 1 374 814 A1 | 1/2004 |
| EP | 2692923 | 2/2014 |
| JP | H1036795 A | 2/1998 |
| JP | H11335960 A | 12/1999 |
| JP | 2001522412 A | 11/2001 |
| JP | 2002273808 A | 9/2002 |
| JP | 2003275093 A | 9/2003 |
| JP | 2008169506 A | 7/2008 |
| JP | 2011038219 A | 2/2011 |
| WO | 98/50611 A1 | 11/1998 |
| WO | WO 2006/048173 | 5/2006 |
| WO | WO 2007/117235 | 10/2007 |
| WO | WO 2012/024576 | 2/2012 |
| WO | WO 2012/134988 | 10/2012 |
| WO | WO-2012134988 A1 * 10/2012 ....... A61F 13/51496 |

\* cited by examiner

NONWOVEN FABRIC AND PROCESS FOR FORMING THE SAME

FIELD OF THE INVENTION

The present invention relates to a nonwoven fabric; a process for forming the nonwoven fabric; an absorbent article comprising the nonwoven fabric; and the use of the nonwoven fabric in an absorbent article.

BACKGROUND OF THE INVENTION

Nonwoven fabrics are widely applied in disposable absorbent articles for personal care or hygiene. In such articles softness and drapability are of great importance since it reassures the wearer or caregiver that the article is experienced as comfortable.

In WO 2012/024576 A1, an absorbent article adapted to be worn about a wearer's lower torso is described which aims to enhance the perceived softness of the absorbent article. The absorbent article described in said document comprises a liquid permeable top sheet, a liquid impermeable back sheet and an absorbent core disposed between the top sheet and the back sheet. The liquid impermeable back sheet comprises a laminate of a wearer-facing layer of liquid impermeable, vapor permeable polymeric film and a garment-facing layer of a nonwoven web. The nonwoven web is being impressed with a first pattern of bond impressions in the shape of diamonds, which first pattern defines a second pattern of unbounded raised regions which also have the shape of diamonds. In this respect reference is made to FIGS. 3A-4B of WO 2012/024576. In the process for manufacturing the nonwoven web a hydroentangling or hydroengorgement process is required to increase loft and/or caliper, enhancing visual and tactile softness signals. A drawback of such hydroentangling or hydroengorgement process is, however, that it adds considerably to the manufacturing costs of the absorbent articles. Moreover, the softness of said absorbent articles leaves room for improvement.

WO 2006/048173 describes a loop-forming nonwoven material for a mechanical closure system. The fabrics are thermally bonded with a first pattern of bond impressions that create a second pattern of larger unbonded raised regions and a third pattern of smaller unbonded areas. The impressions are a combination of trilobally and linearly shaped geometry. This provides a positive impact on the mechanical stability of the fabric but has the disadvantage that it limits the drapability, an important feature for softness perceiveness. In this respect it is remarked that drapability is the extent to which a fabric will deform when it is allowed to hang under its own weight.

The fibers used in the nonwoven materials as described in the above documents are usually made of polyolefins such as polyethylene and in particular polypropylene. In light of environmental constraints it would, however, be desirable to use in absorbent articles for personal care or hygiene biodegradable polymers such as for instance polylactic acid (PLA). Conventional use of PLA-containing fibers in nonwovens results however in nonwoven products having a high stiffness and a low softness, limiting the usefulness of such fibers in hygiene products considerably. In order to deal with these disadvantages, nonwovens with conventional oval elliptic or diamond shaped bonding patterns have been developed that comprise PLA fibers which contain a PLA core and a softer polymer sheath which is made of polyolefins such as polyethylene of polypropylene. Such bi-component PLA fibers have for instance been described in U.S. Pat. No. 6,677,038. Although this approach improves partly the softness, it hardly improves the drapability of the nonwovens due to the stiffness of the core. Increasing the amount of softer polyolefins in the sheath may reduce the overall stiffness of the fibers, but will at the same time affect the degradability of the nonwovens.

Hence, there is a need to develop biodegradable nonwovens that display improved drapability, sufficient shear strength and a high tensile strength.

Object of the present invention is to provide a biodegradable nonwoven fabric suitable for use in absorbent articles which show increased drapability, and thus improved softness, whereas at the same time sufficient shear strength and a high tensile strength are established.

SUMMARY OF THE INVENTION

It has now been found that this can be established when use is made of nonwoven fabrics wherein use is made of a combination of polylactide acid-containing fibers and a particular pattern of bonded and non-bonded areas.

Accordingly, the present invention provides a nonwoven fabric comprising a plurality of polylactic acid-containing fibers that form a nonwoven web, wherein the web has a side which is provided with an alternating pattern of individualized bonded areas which bonded areas are in the form of rods which are arranged in the cross direction of the web, the rods are arranged in such a way that in the machine direction of the web no uninterrupted regions exist along the web while in the cross direction of the web the arrangement of the rods defines a plurality of uninterrupted regions that extend continuously along the web, the alternating pattern of individualized bonded areas defines a non-bonded area, the web has a basis weight on the range of from 5-50 $g/m^2$, the surface of the bonded areas is in the range of 5-20% of the total surface of the side, and the surface of the non-bonded area is in the range of 80-95% of the total surface of the side.

Major advantages of the present invention are the facts that the nonwoven fabric is biodegradable, displays a surprisingly high drapability, i.e. perceived softness, and at the same time sufficient shear strength and a high tensile strength. The fact that the present nonwoven fabrics display a surprisingly high drapability and at the same time a high tensile strength is surprising since it is generally acknowledged that drapability and dimensional stability (i.e. high tensile strength) of a thermobonded nonwoven fabric are features that mutually exclude each other. An additional important advantage is that the present nonwoven fabric allows for a very low overall bonded area whilst at the same time a high amount of biodegradable polylactic acid can be used which significantly improves the drapability of the nonwoven fabric.

It is further known from EP 2 692 923 A1 that nonwoven webs can be made of PLA-containing fibers having a pattern of ribs that are shaped like a stretched S whereby the ribs make particular angles with respect to the cross direction. In WO 2012/134988 A1, a pattern of rods is described whereby the rods run parallel to the machine direction, creating uninterrupted regions in the machine direction along the web, whereas at the same time interrupted regions occur in the cross direction. In WO 2007/117235 A1, reference is made to U.S. Pat. No. 5,620,779 in which a bonding pattern is described that contains uninterrupted in both the machine direction and the cross direction.

DETAILED DESCRIPTION OF THE INVENTION

Figure 1:
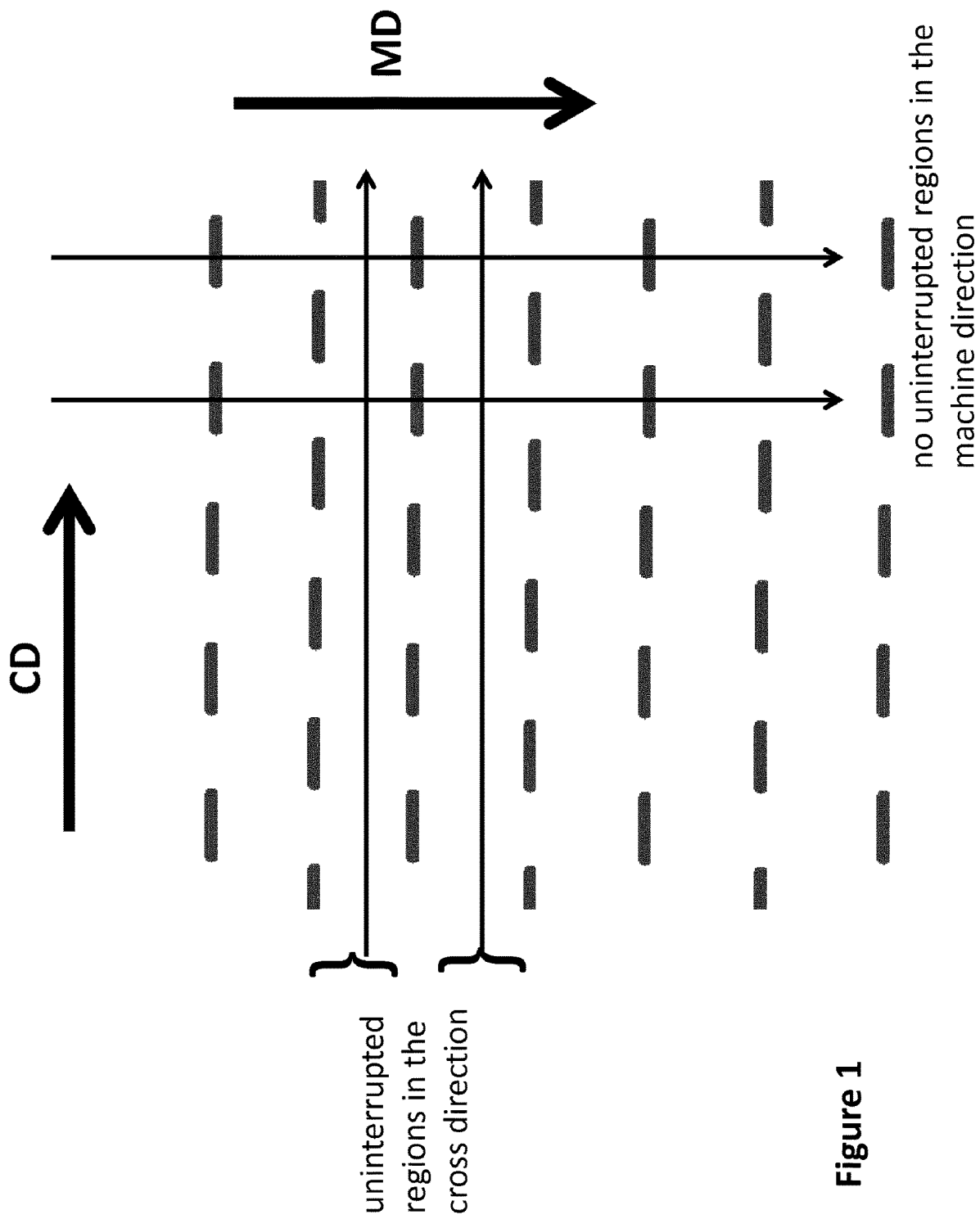
FIG. 1 depicts a bonding pattern having no uninterrupted regions in the machine direction.

In accordance with the present invention the nonwoven fabric comprises a plurality of polylactic acid-containing fibers that form a nonwoven web which comprises a side which is provided with an alternating pattern of individualized bonded areas which bonded areas are in the form of rods which are arranged in the cross direction of the web. The rods are arranged in such a way that in the machine direction of the web no uninterrupted regions exist along the web while in the cross direction of the web the arrangement of the rods defines a plurality of uninterrupted regions that extend continuously along the web. The alternating pattern of individualized bonded areas defines a pattern of non-bonded areas. The web has a basis weight in the range of from 5-50 g/cm$^2$, the surface of the bonded areas is in the range of 5-20% of the total surface of the side, and the surface of the non-bonded area is in the range of from 80-95% of the total surface of the side.

The combination of the particular alternating pattern of individualized bonded areas and the polylactide-containing fibers to be used in accordance with the present invention provides a surprisingly high drapability. Moreover, the large non-bonded area allows for the fiber to bulk up and increase the bulkiness of the fabric. This is perceived as an even higher drapability from both visual and tactile perspective. Preferably, the surface of the non-bonded area is in the range of from 82-93% of the total surface area of the side. More preferably, the surface of the non-bonded area is in the range of from 84-91% of the total surface area of the side. The surface of the bonded areas is preferably in the range of from 7-18% of the total surface area of the side, more preferably in the range of from 9-16% of the total surface area of the side.

Preferably, the alternating pattern consists of the individualized bonded areas which are in the form of rods. Hence, preferably the alternating pattern does not contain additional bonded areas in addition to the rods which are arranged in the cross direction of the web.

The individualized bonded areas are in the form of rods which are arranged in the cross direction of the web. The cross direction is the direction along the web material substantially perpendicular to the direction of forward travel of the web material through the manufacturing line in which the web material is manufactured.

Preferably, the individualized bonded areas in the form of rods each in their length direction form an angle of 90° with the machine direction of the web.

The rods are arranged in such a way that in the machine direction no uninterrupted regions exist along the web, while in the cross direction the arrangement of the rods define a plurality of uninterrupted regions that each extend continuously along the cross direction of the web. The plurality of respective uninterrupted regions are arranged on top of each other in the machine direction of the web. Such an arrangement of the rods results in a number of improved fabric properties.

The skilled person will understand that the phrase "rod" is meant to define a linear straight shape such as a straight bar or stick.

The tensile strength into the cross direction is significantly improved, as the filaments are boldly bound perpendicular to their preferred lay-down direction. It is thereby of importance that no uninterrupted regions in the preferred lay-down direction (i.e. the machine direction) exist, as this would create weak areas of unbonded filaments, resulting in a reduced tensile strength. Moreover, since there are no uninterrupted regions in the machine direction along the web, the free fiber length (i.e. average length of a single fiber between its first and second bond) is comparatively short, resulting in an improved abrasion resistance. Further, this particular arrangement of rods provides uninterrupted unbonded areas along the cross direction of the web, significantly reducing the bending forces of the fabric and translating into an excellent drapability without sacrificing mechanical strength. This finding is surprising because these two properties usually exclude each other.

The width of these uninterrupted regions in the cross direction is suitably larger than 750 μm, and preferably the width is in the range of from 1000-2000 μm. The width of the uninterrupted regions can suitably be determined by means of an appropriate dipstick or screw gauge.

The rods may have flat ends and/or bended ends. Preferably, the bended ends have a circular shape. Preferably, the rods have a linear shape.

Suitably, the individualized bonded areas in the form of rods have a surface in the range of from 0.7-1.5 mm$^2$, preferably in the range of from 0.9-1.3 mm$^2$, and more preferably in the range of from 1.1-1.2 mm$^2$. The surface of the individualized bonded areas can suitably be determined by means of calculation according to the usual mathematical rules from the outer size of the single rod.

The nonwoven web has a basis weight in the range of from 5-50 g/m$^2$, preferably in the range of from 8-40 g/m$^2$, and more preferably in the range of from 10-30 g/m$^2$. The basis weight of the nonwoven web can suitably be determined according to standard methods, such as for example, DIN EN 29073-1 (08/92).

The rods suitably have a maximum width in the range of from 0.1-1.2 mm, preferably in the range of from 0.3-0.8 mm, and more preferably in the range of from 0.4-0.6 mm. The width of the rods can suitably be determined by means of an appropriate dipstick or screw gauge.

The rods suitably have a maximum length in the range of from 1.2-3.5 mm, preferably in the range of from 1.8-3.0 mm, and more preferably in the range of from 2.2-2.6 mm. The length of the rods can suitably be determined by means of an appropriate dipstick or screw gauge.

Suitably, the individualized bonded areas in the form of rods have a length which is 2-10 times, preferably 2-8 times their width.

The discrete non-bonded area suitably has a depth in the range of from 0.1-0.8 mm, preferably in the range of from 0.1-0.6 mm, more preferably in the range of from 0.15-0.5 mm, and most preferably in the range of from 0.15-0.4 mm. The depth can suitably be determined by means of an appropriate dipstick or screw gauge.

Suitably, the distance between each pair of adjacent rods is in the range of from 1.8-3.0 mm, preferably 2.2-2.6 mm in the cross direction. Suitably, distance between each pair of adjacent rods is in the range of from 2.5-5.0 mm, preferably 3.3-4.2 mm in the machine direction. In this respect it is observed that the machine direction is the direction along the web material substantially parallel to the direction of forward travel of the web material through the manufacturing line in which the web material is manufactured. The distance can suitably be determined by means of an appropriate dipstick or screw gauge.

Suitably, the nonwoven web according to the present invention has a tensile strength according WSP 110.4 in MD (Machine Direction) in the range of from 0.4-2.4 N per gram basis weight, preferably in the range of from 0.5-2.2 N per gram basis weight, and more preferably in the range of from 0.6-2.0 N per gram basis weight.

Suitably, the nonwoven web according to the present invention has a tensile strength according WSP 110.4 in CD (Cross Direction) in the range of from 0.1-1.2 N per gram basis weight, preferably in the range of from 0.2-1.0 N per gram basis weight, and more preferably in the range of from 0.3-0.9 N per gram basis weight.

Non-woven webs with such tensile strengths provide non-woven articles with a high tensile strength. This WSP test method is an internationally acknowledged test method in the nonwoven industry, as the skilled person will understand.

In accordance with the present invention use is made of polylactic acid-containing fibers.

Polylactic acid (PLA) is an environmentally friendly organic material, which is made from vegetable renewable raw materials such as sugars from food crops such as maize, sugar beet, sugar cane) and wheat or cellulose. Polylactic acid has the advantage that it is biodegradable and will dissolve into carbon dioxide, biomass and water. In addition, polylactic acid is recyclable. Polylactic acid is mainly formed from the monomers lactic acid, and the cyclic di-ester, lactide. Polylactic acid is usually formed by means of ring-opening polymerization of lactide using a metal catalyst such as for instance tin octoate. Another process to form polylactic acid involves the direct condensation of lactic acid monomers.

In the context of the present patent application the term "biodegradable" is meant to define a product which degrades or decomposes under environmental conditions.

The nonwoven fabric may also contain in addition to the polylactic acid material other polymer material such as polypropylene, polyethylene and its copolymers, aliphatic and aromatic polyesters, and combinations thereof. One specific embodiment of the invention makes use of employing two different types of polylactic acid in the fiber. Further, the nonwoven fabrics may also comprise natural fibers such as wood, cotton, or rayon in combination with thermoplastic fibers. The nonwoven web may also be a composite made up of a mixture of two or more different fibers or a mixture of fibers and particles. Suitably, the polylactic acid-containing fibers are present in an amount of at least 30 wt %, based on the total amount of fibers in the nonwoven fabric. Preferably, the polylactic acid-containing fibers are present in an amount of at least 50 wt %, more preferably at least 75 wt %, based on the total amount of fibers in the nonwoven fabric. Most preferably, the nonwoven fabric only contains polylactic-containing fibers.

Preferably, the additional fiber component is formed from a different polylactic acid, polyethylene or polypropylene homopolymers, co-polymers thereof, blends of polyethylene and polypropylene, polyester, co-polymers of polyesters and/or blends of polyesters.

In the case of propylene-based polymers the polymers may comprise co-monomer-derived units selected from ethylene and C4-C10 α-olefins. In the case of ethylene-based polymers the polymers may comprise co-monomer-derived units selected from C3-C10 α-olefins. Suitable examples of polyolefin materials include propylene homopolymers, ethylene homopolymers, propylene copolymers and ethylene copolymers such as linear low density polyethylene (LLDPE), high density polyethylene (HDPE), and low density polyethylene (LDPE).

Suitable polyesters can be aliphatic polyesters such as, e.g. polylactic acid, or aromatic polyesters such as polyethylene terephthalate (PET) and poly(trimethylene terephthalate (PTT).

In one embodiment of the present invention, the additional polymer material which is to be used in the polylactic acid-containing fibers is a bio-polyethylene polymer, also known as green polyethylene or renewable polyethylene. Such a polyethylene is made out of ethanol, which becomes ethylene after a dehydration process. It can be made from various feedstocks including sugar cane, sugar beet, and wheat grain. The final polyethylene product so obtained has identical properties to polyethylene that is produced from petrochemical sources.

The melt flow rate (MFR) of the polylactic acid material to be used in the present invention is suitably less than 100 dg/min. The MFR is determined using ASTM test method D1238, 2.16 kg. Preferably, the MFR of the polylactic acid material is in the range of from 5-90 dg/min, more preferably in the range of from 15-65 dg/min.

The polylactic acid-containing fibers to be used in accordance with the present invention suitably have a tex of less than 6 dtex, preferably less than 4 dtex. A tex is a metric measure of the weight per unit of a fiber. It is numerically equal to the weight in grams of ten kilometer (10000 meters) of the fiber.

The polylactic acid-containing fibers to be used in accordance with the present invention may in addition contain a slip agent. The use of a slip agent in combination with the particular pattern of rods and the polylactic acid-containing fibers brings about a surprisingly high drapability and thus perceived softness.

The slip agent is suitably added to the polylactic acid material during the manufacturing process of the fabric, e.g. in form of a masterbatch during the spinning process.

The slip agent to be used in accordance with the present invention can be any slip agent which can suitably be used in the manufacturing of nonwoven fabrics. It can be an internal slip agent, which usually is compatible with the polymer matrix, or it can be an external slip agent that migrates to the fiber surface due to a certain incompatibility with the polymer matrix. Suitably, the slip agent can be a hydrocarbon compound or a fatty acid derivative having one or more functional groups selected from alcohols, carboxylic acid, aryls and substituted aryls, alkoxylates, esters, amides. Slip agents also can be fatty acid esters of multivalent alcohols, compounds comprising unsaturated C—C bonds, oxygen, nitrogen, or a compound based on a silicone-containing compound.

Typical examples of specifically attractive slip agents are for example, polyethylene and polypropylene waxes, primary and secondary amides such as for instance erucamide and oleamide, and stearyl derivatives.

The slip agent is suitably present in an amount in the range of from 0.1-5 wt %, preferably in an amount of 0.5-3 wt %, based on the total weight of the polypropylene-containing fibers.

Besides additives already contained in the employed polymers, addition of further additives is possible to provide additional properties to the fibers. Suitable further additives include thermal stabilizers, light stabilizers, waxes, and additives to make the fabrics either hydrophilic or hydrophobic. For the sake of esthetics, the fibers can be pigmented with a color pigment. The addition of filler materials can sometimes also be of advantage. Suitable filler materials include organic and inorganic filler materials. Suitable examples of inorganic filler materials include minerals such as calcium carbonate, metals such as aluminium and stainless steel. Suitable examples of organic filler materials include sugar-based polymers.

Various fiber cross-sections are possible. A round fiber cross-section is preferred, but also tri- and multilobal shaped fibers can advantageously be used. Other suitable fiber cross-sections include triangular, bone-shaped, moon-shaped, hollow-fibers, and ribbon-shaped cross-sections.

The fibers from which the nonwoven webs are made can suitable be single component or multicomponent fibers such as bicomponent fibers. Suitable examples of multicomponent fibers include symmetric and eccentric core/sheath fibers, side-by-side fibers of A/B or A/B/A-structure, segmented pie fibers, island-in-a-sea fibers, and striped fibers. Preferred are bicomponent fibers where the two components are arranged in a symmetric core-sheath way or in a side-by-side way. Most preferred are core-sheath bicomponent fibers. The bicomponent fibers will contain two polymer components, a first component which comprises the polylactic acid material and a second component that contains either a different polylactic acid material or a polymer material such as for instance a polyolefin or polyester. The second component is suitably made of a softer (i.e. lower melting) polymer material, for example polyethylene and polypropylene, when compared with the polylactic acid component. Suitably, for core-sheath fibers, the core comprises the polylactic acid-containing component and the sheath comprises the component with the lower melting point such as polyethylene or polypropylene. In another embodiment the sheath comprises the polylactic acid-containing component and the core comprises the component with the lower melting point such as polyethylene or polypropylene. In both embodiments the polyolefin to be used is preferably a polypropylene. In a preferred embodiment, the bicomponent fiber has a core of polylactic acid material and a sheath of polyolefin material. In preferred embodiments, the bicomponent fiber comprises from 10% to 90% by weight of the polylactic acid-containing component in the core and from 90% to 10% by weight of a lower melting component such as polyethylene or polypropylene in the sheath. Most preferably, the bicomponent fiber has from 30% to 70% by weight of the polylactic acid-containing component in the core. The bicomponent fibers may also contain different types of polylactic acid materials. In such an embodiment, the bicomponent fiber has a core of a polylactic acid material and a sheath of a polylactic acid material which differs in physical properties from the first material.

In another embodiment, a side-by-side-bicomponent fiber comprises two polylactic acid materials that differ in melt temperature or melt flow or other physical properties. Also in such bicomponent fibers, a first component can comprise a polylactic acid and a second component which comprises a polyolefin or polyester as indicated before.

Especially preferred polyolefins to be used in the bicomponent fibers in accordance with the present invention include propylene homo- and copolymers, as well as ethylene homo- and copolymers. The polyolefins can also consist of blends, e.g. of two polypropylenes which differ in physical properties or e.g. a mixture of polypropylene with polyethylene.

The polylactic acid-containing fibers are suitably joined by bonding to form a coherent web structure. Suitable bonding techniques include, but are not limited to, chemical bonding and thermal bonding, for example thermal calendering or bonding by a hot gas stream. Also ultrasonic welding is possible. In a very preferred embodiment use is made of thermal calendering with the aforementioned specific bond pattern.

The nonwoven fabrics in accordance with the present invention may be produced by any of the known processes for making a nonwoven fabric.

The nonwoven fabric may be a single layer or multi-layer nonwoven fabric having, for example, at least one layer of a spunbond web joined to at least one layer of a meltblown web, a carded web, or other suitable material. Suitably, the nonwoven fabric according to the present invention comprises additional nonwoven webs.

Suitable multi-layer fabrics may include one or more spunbond layers (S) and meltblown layers (M), such as SMS, SMMS, SSMMS, etc. adhered to a nonwoven fabric according to the present invention. Usually, these multilayer fabrics are made in one step on a single line with multiple beams, which generally encompass a combination of spunbond and meltblown beams. In some cases it might be advantageous or technically necessary to make a multiple layer according to the invention in two or more separate steps.

The nonwoven webs may be extensible, elastic, or non-elastic. The nonwoven webs may be spunbond webs, meltblown webs, air-laid webs, or carded webs. If the nonwoven web is a web of meltblown fibers, it may include meltblown microfibers. The nonwoven fabric in accordance with the present invention may comprise one or more spunbond webs and one or more meltblown webs. The polylactic acid-containing fibers can be made according to spinning technologies known in the art. Most conveniently employed are spunbond and meltblown processes, from which the nonwoven fabrics can directly be formed.

Spunbond fibers are generally produced by extruding a molten polymer through a large spinneret having several thousand holes per linear meter or from banks of smaller spinnerets, for example, containing as few as 40 holes. After exiting the spinneret, the molten fibers are quenched by a cross-flow air quench system, then pulled away from the spinneret and attenuated by high speed air. Lay-down of the filaments to create a nonwoven layer occurs on a permeable transport belt. Spunbond fibers are generally continuous and range in fiber diameter between ca. 10-100 µm.

The use of spunbond layers that differ in their fiber cross-section or in their fiber type are possible. Thus, it is also possible to combine a layer of trilobal filaments with a layer of round fibers, or to combine a core-sheath bicomponent layer with a side-by-side bicomponent layer.

A meltblowing process is a process in which fibers are formed by extruding a molten thermoplastic material through a plurality of fine, usually circular die capillaries as molten threads or filaments into a high velocity, usually heated gas streams, which attenuate the filaments of molten thermoplastic material to reduce their diameter. The meltblown process normally has the filaments in single row of filaments across the width of the die. Thereafter, the meltblown fibers are carried by the high velocity gas stream and are deposited on a collecting surface to form a web of randomly dispersed meltblown fibers.

Meltblown fibers on the other hand are generally much smaller in diameter and usually range between 0.5-10 µm. Additionally, meltblown fibers are considered to be mainly discontinuous.

The nonwoven fabric in accordance with the invention can additionally be treated to add specific properties. Most common are topical treatments to make the fabric either hydrophilic or to make it hydrophobic. Most common is the treatment of the fabric with hydrophilic surfactants. In the context of the present invention a surface of a nonwoven fabric or nonwoven web is "hydrophilic" when the contact angle of water disposed on that surface is less than about 90 and a surface is "hydrophobic" when the contact angle of water disposed on that surface is greater than or equal to 90.

The present invention also relates a process for forming a nonwoven fabric according to the present invention comprising the steps of:
(a) forming a nonwoven web of a plurality of polylactic acid-containing fibers; and
(b) feeding the nonwoven web into a nip defined between oppositely positioned first and second rolls, whereby at least one of the rolls has a patterned outer surface to apply a bonding pattern to the first nonwoven web, whereby the bonding pattern comprises the alternating pattern of the individualized bonded areas and the non-bonded area as defined hereinbefore.

Further, the present invention also relates to a process for forming a nonwoven fabric according to the present invention comprising the steps of:
(a) forming a first nonwoven web of a plurality of polylactic acid-containing fibers;
(b) forming a second nonwoven web;
(c) forming a third nonwoven web;
(d) feeding the first nonwoven web, second nonwoven web and the third nonwoven web into a nip defined between oppositely positioned first and second rolls, whereby at least one of the rolls has a patterned outer surface to apply a bonding pattern to the first nonwoven web, whereby the bonding pattern comprises the alternating pattern of bonded areas and the non-bonded area as defined hereinbefore; and
(e) bonding the first, second and third nonwoven web together to form the nonwoven fabric.

Preferably, in these processes the forming of the one or more nonwoven webs is carried out by means of a spunbond process or a meltblown process.

Accordingly, the present invention also relates a process for forming a nonwoven fabric according to the present invention comprising the steps of:
(a) forming a nonwoven web of polylactic acid-containing fibers by means of a spunbond process or a meltblown process; and
(b) feeding the nonwoven web into a nip defined between oppositely positioned first and second rolls, whereby at least one of the rolls has a patterned outer surface to apply a bonding pattern to the first nonwoven web, whereby the bonding pattern comprises the alternating pattern of the individualized bonded areas and the non-bonded area as defined hereinbefore.

Further, the present invention also relates to a process for forming a nonwoven fabric according to the present invention comprising the steps of:
(a) forming a first nonwoven web of a plurality of polylactic acid-containing fibers by means of a spunbond process or a meltblown process;
(b) forming a second nonwoven web by means of a spunbond process or meltblown process;
(c) forming a third nonwoven web by means of a spunbond process or meltblown process;
(d) feeding the first nonwoven web, second nonwoven web and the third nonwoven web into a nip defined between oppositely positioned first and second rolls, whereby at least one of the rolls has a patterned outer surface to apply a bonding pattern to the first nonwoven web, whereby the bonding pattern comprises the alternating pattern of bonded areas and the non-bonded area as defined hereinbefore; and
(e) bonding the first, second and third nonwoven web together to form the nonwoven fabric.

In addition to the first nonwoven web, the second and/or third nonwoven web may also suitably be formed of a plurality of polylactic acid-containing fibers.

Accordingly, the present invention also relates to a process for forming a nonwoven fabric according to the present invention comprising the steps of:
(a) forming a first nonwoven web of a plurality of polylactic acid-containing fibers by means of a spunbond process or a meltblown process;
(b) forming a second nonwoven web of a plurality of polylactic acid-containing fibers by means of a spunbond process or meltblown process;
(c) forming a third nonwoven web of a plurality of polylactic acid-containing fibers by means of a spunbond process or meltblown process;
(d) feeding the first nonwoven web, second nonwoven web and the third nonwoven web into a nip defined between oppositely positioned first and second rolls, whereby at least one of the rolls has a patterned outer surface to apply a bonding pattern to the first nonwoven web, whereby the bonding pattern comprises the alternating pattern of bonded areas and the non-bonded area as defined hereinbefore; and
(e) bonding the first, second and third nonwoven web together to form the nonwoven fabric.

In a particular attractive embodiment of the present invention a first and third nonwoven webs are formed of a plurality of polylactic acid-containing fibers by means of a spunbond process, and a second nonwoven web is formed of a plurality of polylactic acid-containing fibers by means of a meltblown process.

Accordingly, the present invention also relates to a process for forming a nonwoven fabric according to the present invention comprising the steps of:
(a) forming a first nonwoven web of a plurality of polylactic acid-containing fibers by means of a spunbond process;
(b) forming a second nonwoven web of a plurality of polylactic acid-containing fibers by means of a meltblown process;
(c) forming a third nonwoven web of a plurality of polylactic acid-containing fibers by means of a spunbond process;
(d) feeding the first nonwoven web, second nonwoven web and the third nonwoven web into a nip defined between oppositely positioned first and second rolls, whereby at least one of the rolls has a patterned outer surface to apply a bonding pattern to the first nonwoven web, whereby the bonding pattern comprises the alternating pattern of bonded areas and the non-bonded area as defined hereinbefore; and
(e) bonding the first, second and third nonwoven web together to form the nonwoven fabric.

An important advantage of the present process for forming the nonwoven fabrics in accordance with the present invention is the low neck-in which is realized. In this respect it is observed that a low neck-in is important since webs that show neck-in will distort to become longer in the machine direction and shorter in the cross-machine direction when they are converted into products. Therefore, neck-in creates a difficult process to control, especially in achieving the desired width of the facing of the finished laminate. It is therefore surprising that in accordance with the present invention a low neck-in can be realized, whereas at the same time a nonwoven web is formed having a low basis weight.

The rolls to be used in the processes according to the present invention are suitably right circular cylinders that can be formed of any suitable, durable material. Such rolls will be operated in ways known in the art.

The locations of the oppositely positioned rolls can suitably be varied to form the nip between the rolls. The nip pressure within nip can suitably be varied depending upon the properties of the one or more nonwoven webs to be processed. The same is true for the necessary temperature of the calender rolls, which has to be adjusted according to the required final properties and the kind of fibers to be bonded.

The bonded areas are suitably formed by means of melt-fusing by controlling the temperature of at least one of the rolls. The temperature of the outer surface of at least one of the rolls can be adjusted by heating or cooling the rolls. The heating and cooling may affect the features of the web(s) being processed and the degree of bonding of single or multiple webs being passed through the nip formed between the respective rolls. In the present process, the rollers are suitably heated up to a temperature in the range of from 110 to 190° C. and a pressure is applied in the range of from 50 to 100 N/mm.

One of the rolls to be used will contain a bonding pattern on its outermost surface comprising a continuous pattern of land areas defining a plurality of discrete openings, apertures or holes. Each of the openings in the one or more rolls will form a discrete unbonded area in at least one side of the nonwoven fabric or nonwoven web. The other roll will suitably have an outer surface which is much smoother than the other roll. Preferably, the outer surface of the other roll will be smooth or flat. The rotational speeds of the respective rolls are substantially identical.

The present invention also relates to an absorbent article comprising a nonwoven fabric according to the present invention. Suitably, the absorbent article according to the present invention is a disposable hygiene absorbent article selected from the group consisting of incontinence articles, diapers, wipes and fem-care articles. Suitable disposable hygiene absorbent articles according to the present invention include those selected from the group consisting of baby diapers, pull-ups, training pants, hygiene closure systems, wipes, fem-care articles, and adult incontinence briefs and diapers. Preferably, the absorbent article in accordance with the present invention is an adult incontinence article such as an incontinence brief or diaper.

Disposable absorbent articles are absorbent articles which are not intended to be laundered or otherwise restored or reused as absorbent articles. Generally, such absorbent articles comprise a back sheet, a top sheet and an absorbent core which is arranged between the back sheet and the top sheet. An additional function of the top sheet is to provide skin comfort.

The nonwoven fabric according to the present invention can suitably be part of a top sheet, back sheet, landing zone and/or a waist belt, wing or a frontal ear.

Preferably, the present nonwoven fabric is part of a closure system in adult incontinence article, preferably a waist belt, wing or frontal ear.

The present invention also relates to the use of the nonwoven fabric according to the present invention in an absorbent article. Preferably, in such a use the absorbent article is a hygiene absorbent article selected from the group consisting of baby diapers, pull-ups, training pants, hygiene closure systems (e.g. diaper closure tabs), wipes, fem-care articles, and adult incontinence briefs and diapers.

The present invention also relates to the use of the present nonwoven fabric in a hygiene absorbent article, wherein the nonwoven fabric forms at least part of the back sheet and/or top sheet of the hygiene absorbent article.

In FIG. 1, a bonding pattern in accordance with the present invention is shown. The bonding pattern comprises individualized bonded areas in the form of rods in the cross direction of the web which define a non-bonded area, whereby the rods are arranged in such a way that in the machine direction of the web no uninterrupted regions exist along the machine direction of the web while in the cross direction of the web the arrangement of the rods defines a plurality of uninterrupted regions that each extend continuously along the cross direction of the web,

EXAMPLES

In these Examples, a comparison is made between nonwoven fabrics comprising a polylactic acid polymer that are bonded with standard calenders providing bonded areas of an elliptic shape, and nonwoven fabrics in accordance with the present invention which are bonded with the particular calender pattern of bonded areas in the form of rods in accordance with the present invention. All the nonwoven fabrics consisted of bicomponent (core/sheath) fibers in which the core was made of polylactid acid (PLA) and the sheath was made of polypropylene (PP) or polyethylene (PE). All the nonwoven fabrics used were made by a spunbond process as provided, e.g. by a Reicofil spunbond line. Reicofil is the name of the spinning lines offered by Reifenhauser GmbH & Co. KG, Germany, which are well known to those skilled in the art.

A bicomponent set-up of a spinning line requires two separate extruders and spinning pump systems. The first extruder is handling the polymer for the core, while the second extruder is handling the polymer for the sheath. In the extruders, the polymers are melted and transported, while the spinning pumps press the polymer melt through orifices of a spinning plate to form polymer threads. Such a spinning plate can consist of several thousand holes. The obtained polymer thread is cooled, drawn, and randomly laid down on a transporting belt. This fiber mat of unconsolidated fibers is then passed through a calender to be thermally bonded and to result in the final nonwoven fabric.

The tensile strength is measured according to WSP 110.4 on a ZWICK tensile tester.

The stiffness of the respective nonwoven fabrics is measured with a Handle-O-Meter according to IST 90.03 (INDA standard test). The values are reported in mN. This value is proportional to the stiffness, which means, the higher the value the stiffer is the material.

Examples 1a, 2a, 3a and 4a (Comparative Examples)

Figure 2:
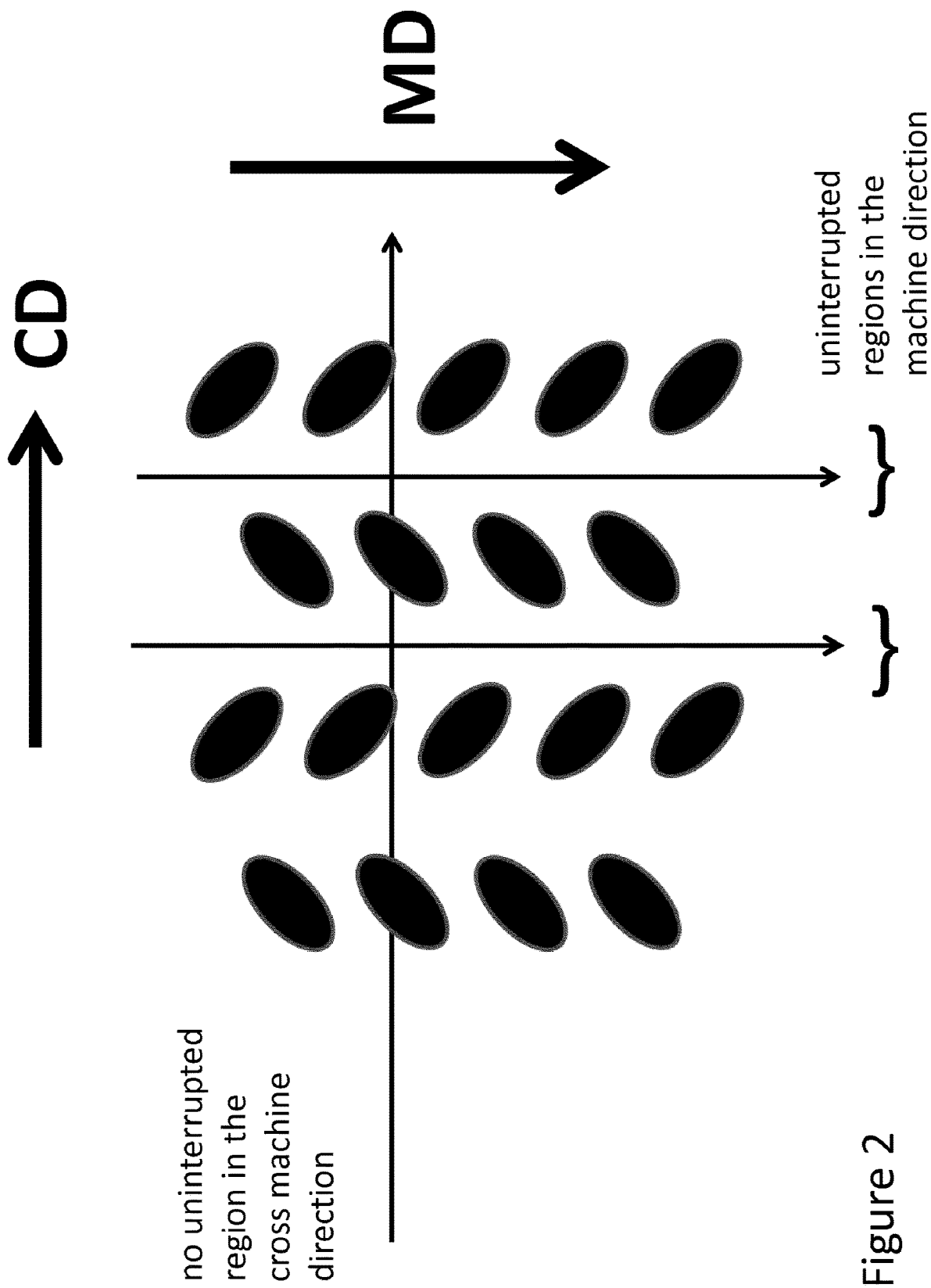
FIG. 2 depicts a bonding pattern having interrupted regions in the machine direction.

In these Examples, a nonwoven web is prepared from a nonwoven fabric comprising a polylactic acid polymer. The bonding pattern consists of bonded areas having an elliptic shape, and is shown in FIG. 2. As will be clear from FIG. 2, in this comparative bonding pattern there do not exist uninterrupted regions in the cross direction of the web that extend continuously along the cross direction of the web. However, in the machine direction of the web there do exist uninterrupted regions that extend continuously along the machine direction of the web. The surface of the bonded areas was 18%, based on the total surface.

Example 1b, 2b, 3b and 4b (According to the Invention)

In these Examples, a nonwoven web is prepared by a nonwoven fabric comprising a polylactic acid polymer. The bonding pattern consists of rods according to the invention, and is shown in FIG. 1. The surface of the bonded areas was 11%, based on the total surface.

In Tables 1-4, the basic weight (gsm) of the nonwoven webs as prepared according to the respective Examples are shown, as well as the compositions of the bicomponent (core/sheath) fibers of which the respective nonwoven webs were made.

TABLE 1

| 17 gsm core/sheath 50/50 PLA/PP | Example 1a | Example 1b |
|---|---|---|
| Tensile strength MD | 25 | 22 |
| Tensile strength CD | 15 | 13 |
| Handle-O-Meter MD | 140 | 90 |
| Handle-O-Meter CD | 62 | 41 |

TABLE 2

| 20 gsm core/sheath 50/50 PLA/PP | Example 2a | Example 2b |
|---|---|---|
| Tensile strength MD | 30 | 28 |
| Tensile strength CD | 14 | 13 |
| Handle-O-Meter MD | 185 | 123 |
| Handle-O-Meter CD | 70 | 42 |

TABLE 3

| 17 gsm core/sheath 50/50 PLA/PE | Example 3a | Example 3b |
|---|---|---|
| Tensile strength MD | 18 | 16 |
| Tensile strength CD | 7 | 5 |
| Handle-O-Meter MD | 64 | 32 |
| Handle-O-Meter CD | 14 | 9 |

TABLE 4

| 20 gsm core/sheath 50/50 PLA/PE | Example 4a | Example 4b |
|---|---|---|
| Tensile strength MD | 20 | 18 |
| Tensile strength CD | 9 | 7 |
| Handle-O-Meter MD | 86 | 42 |
| Handle-O-Meter CD | 52 | 19 |

It will be clear from Tables 1-4, that all the Examples in accordance with the present invention (Examples 1b, 2b, 3b and 4b) display a lower stiffness and thus improved drapability while at the same time nearly maintaining the tensile strength when compared to the comparative Examples that are not according to the invention (Examples 1a, 2a, 3a and 4a). In addition, the fact that the present nonwoven fabrics display a surprisingly high drapability and at the same time maintain a high tensile strength is surprising since it is generally acknowledged that drapability and dimensional stability (i.e. high tensile strength) of a thermobonded nonwoven fabric are features that mutually exclude each other.

The invention claimed is:

1. A nonwoven fabric comprising a plurality of polylactic acid-containing fibers that form a nonwoven web, which fibers are boldly bound perpendicular to the machine direction, wherein the web has a side which is provided with an alternating pattern of individualized bonded areas which bonded areas are in the form of rods that have a linear shape, the rods having a length and a width, wherein the length is 2-10 times the width, and wherein the rods are arranged in the cross direction of the web, wherein the rods each in their length direction form an angle of 90° with the machine direction of the web, and the rods are arranged in such a way that in the machine direction of the web no uninterrupted regions exist along the web while in the cross direction of the web the arrangement of the rods defines a plurality of uninterrupted regions that extend continuously along the web, the alternating pattern of individualized bonded areas defines a non-bonded area, the web has a basis weight on the range of from 5-50 g/m², the surface of the bonded areas is in the range of 5-20% of the total surface of the side, and the surface of the non-bonded area is in the range of 80-95% of the total surface of the side, and wherein the distance between each pair of adjacent rods in the cross direction is from 1.8 to 3.0 mm, and the distance between each pair of adjacent rods in the machine direction is from 3.3 to 4.2 mm.

2. A nonwoven fabric according to claim 1, wherein the polylactic acid-containing fibers are bicomponent fibers in a sheath-core configuration which comprise a first component that forms the core and a second component that forms the sheath.

3. A nonwoven fabric according to claim 2, wherein the first component comprises polylactic acid and the second component comprises a polyethylene, a polypropylene or a polylactic acid.

4. A nonwoven fabric according to claim 1, wherein the surface of the bonded areas is in the range of from 7-18% of the total surface area of the side.

5. A nonwoven fabric according to claim 1, wherein the surface of the non-bonded area is in the range of from 82-93% of the total surface area of the side.

6. A nonwoven fabric according to claim 1, wherein the fibers have a tex of less than 6 dtex.

7. A nonwoven fabric according to claim 1, wherein the nonwoven web has a basis weight of 8-40 g/m².

8. A nonwoven fabric according to claim 1 comprising one or more additional nonwoven webs.

9. A process for forming a nonwoven fabric according to claim 1 comprising the steps of:
   (a) forming a nonwoven web of a plurality of polylactic acid-containing fibers; and
   (b) feeding the nonwoven web into a nip defined between oppositely positioned first and second rolls, whereby at least one of the rolls has a patterned outer surface to apply a bonding pattern to a side of the nonwoven web, whereby the bonding pattern comprises said alternating pattern of the individualized bonded areas and said non-bonded area.

10. A process for forming a nonwoven fabric according to claim 8 comprising the steps of:
   (a) forming a first nonwoven web of a plurality of polylactic acid-containing fibers;
   (b) forming a second nonwoven web;
   (c) forming a third nonwoven web;
   (d) feeding the first nonwoven web, second nonwoven web and the third nonwoven web into a nip defined between oppositely positioned first and second rolls, whereby at least one of the rolls has a patterned outer surface to apply a bonding pattern to a side of the first nonwoven web, whereby the bonding pattern comprises said alternating pattern of bonded areas and said non-bonded area; and
   (e) bonding the first, second and third nonwoven web together to form the nonwoven fabric.

11. A process according to claim 10, wherein at least one of the three nonwoven webs is made by a spunbond process or a meltblown process.

12. A hygiene absorbent article comprising the nonwoven fabric according to claim 1.

13. The hygiene absorbent article according to claim 12, wherein the nonwoven fabric forms at least part of the back sheet and/or top sheet of the hygiene absorbent article.

14. An absorbent article comprising a nonwoven fabric according to claim 1.

15. An absorbent article according to claim 14, wherein the absorbent article is a hygiene absorbent article selected from the group consisting of baby diapers, pull-ups, training pants, hygiene closure systems, adult incontinence briefs and diapers.

16. A nonwoven fabric according to claim 1, wherein the lengths of the rods is 2-8 times the widths of the rods.

17. A nonwoven fabric according to claim 1, wherein widths of said uninterrupted regions in the cross direction is from about 1000 to 2,000 μm.

\* \* \* \* \*